United States Patent

Stölzer et al.

[11] B 3,993,717
[45] Nov. 23, 1976

[54] S-(ALKOXYCARBONYL)-ALKYL-THIO-PHOSPHORIC ACID ESTER AMIDES

[75] Inventors: Claus Stölzer, Wuppertal; Wolfgang Behrenz; Ingeborg Hammann, both of Cologne, all of Germany

[73] Assignee: Bayer Aktiengesellschaft, Leverkusen, Germany

[22] Filed: Aug. 8, 1973

[21] Appl. No.: 386,673

[44] Published under the second Trial Voluntary Protest Program on February 3, 1976 as document No. B 386,673.

[30] Foreign Application Priority Data

Aug. 16, 1972 Germany............................ 2240033

[52] U.S. Cl................................. 260/942; 260/941; 424/212
[51] Int. Cl.$^2$....................... C07F 9/24; A01N 9/36
[58] Field of Search............................ 260/941, 942

[56] References Cited
UNITED STATES PATENTS 3,019,250   1/1962   Kayser et al..................... 260/941 X
3,705,928   12/1972  Stolzer et al.................... 260/941 X

FOREIGN PATENTS OR APPLICATIONS 1,067,016   10/1959   Germany.......................... 260/941

*Primary Examiner*—Anton H. Sutto
*Attorney, Agent, or Firm*—Burgess, Dinklage & Sprung

[57] ABSTRACT

S-(alkoxycarbonyl)-alkyl-thiophosphoric acid ester amides of the general formula

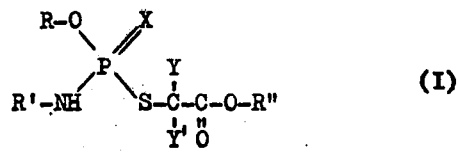

in which
R, R' and R'' each independently is alkyl of 1 to 10 carbon atoms or lower alkenyl,
Y is hydrogen or lower alkyl,
Y' is hydrogen, lower alkyl or —CH$_2$—CO—OR'',
and
X is oxygen or sulfur,
which possess insecticidal and acaricidal properties.

8 Claims, No Drawings

S-(ALKOXYCARBONYL-ALKYL-THIOPHOSPHORIC ACID ESTER AMIDES

The present invention relates to and has for its objects the provision of particular new S-(alkoxycarbonyl)-alkyl-thiophosphoric acid ester amides, i.e. S-(alkoxycarbonyl)-methyl-O-alkyl-N-alkyl-thiol- or -dithio-phosphoric acid ester amides, S-(alkenoxy-carbonyl)-, O-alkenyl- and/or N-alkenyl counterparts, which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from French Patent 1,133,785 that S-(alkoxycarbonyl)-methyl-thiophosphoric acid O,O-dialkyl esters, for example S-(ethoxycarbonyl)-methyl-dithiophosphoric acid, O,O-diethyl ester (Compound A), possess an insecticidal and acaricidal activity.

The present invention provides, as new compounds, the S-(alkoxycarbonyl)-alkyl-thiophosphoric acid ester amides of the general formula

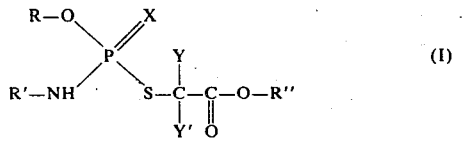

in which

R, R' and R'' each independently is alkyl of 1 to 10 carbon atoms or lower alkenyl, Y is hydrogen or lower alkyl, Y' is hydrogen or lower alkyl or —CH$_2$—COOR'', and X is oxygen or sulfur.

Preferably, R and R' are identical or different, straight-chain or branched lower alkyl with 1 to 4 carbon atoms, or allyl; R'' is straight-chain or branched alkyl with 1 to 8 carbon atoms, or allyl; Y is hydrogen or methyl; and Y' is hydrogen, methyl or —CH$_2$—CO—OR''.

Surprisingly, the new S-(alkoxycarbonyl)-alkyl-thiophosphoric acid ester amides of the formula (I) possess a substantially better insecticidal and acaricidal action than the prior-art S-(alkoxycarbonyl)-methyl-thiophosphoric acid, O,O-dialkyl esters of analogous structure and identical type of action. The compounds according to the invention thus represent an enrichment of the art.

The present invention also provides a process for the preparation of an S-(alkoxycarbonyl)-alkyl-thiophosphoric acid ester amide of the formula (I) in which an O-alkyl-N-monoalkylamido-thiophosphoric acid salt of the general formula

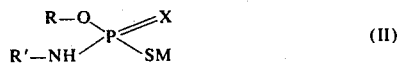

is reacted with a halogenocarboxylic acid alkyl ester of the general formula

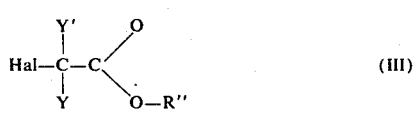

in which formulas

R, R', R'', X, Y and Y' have the meanings stated above,

Hal is halogen, preferably bromine or chlorine, and

M is an alkali metal equivalent, alkaline earth metal equivalent or optionally alkyl-substituted ammonium equivalent.

If the potassium salt of O-ethyl-N-monoisopropylamido-dithiophosphoric acid and chloroacetic acid isopropyl ester are used as starting materials, the course of the reaction can be represented by the following equation:

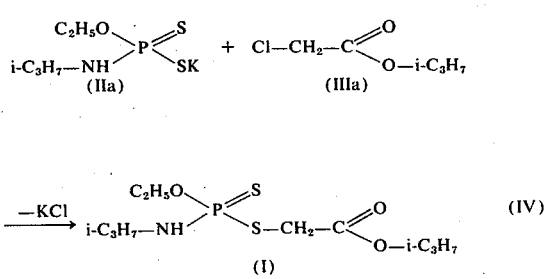

The following may be mentioned as examples of O-alkyl-N-monoalkylamido-thiophosphoric acid salts (II) which can be used: the alkali metal salts, alkaline earth metal salts or optionally alkyl-substituted ammonium salts of O-methyl-N-methyl-, O-methyl-N-ethyl-, O-methyl-N-propyl-, O-methyl-N-isopropyl-, O-ethyl-N-methyl-, O-ethyl-N-ethyl-, O-ethyl-N-propyl-, O-propyl-N-methyl-, O-isopropyl-N-methyl-, O-propyl-N-isopropyl-, O-isopropyl-N-isopropyl-, O-butyl-N-methyl-, O-butyl-N-isopropyl-, O-sec.-butyl-N-isopropyl-, O-allyl-N-methyl-, and O-ethyl-N-allylamido-mono- and -dithiophosphoric acids. These salts can be obtained from the corresponding O-alkyl-N-monoalkylamido-thionophosphoric acid halides and hydrogen sulfide under alkaline conditions or by means of alkali hydroxide solutions.

The halogenocarboxylic acid esters (III) also required as starting materials are known and are obtainable according to customary methods.

The preparative process is preferably carried out with conjoint use of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, such as diethyl ether, dibutyl ether and dioxane; ketones, for example acetone, methyl ethyl ketone, methyl isopropyl ketone and methyl isobutyl ketone; nitriles, for example acetonitrile and propionitrile; and alcohols, such as methanol, ethanol and isopropanol. Water is in certain cases also suitable as a solvent.

The reaction temperature can be varied within a fairly wide range. In general, the reaction is carried out at from 0° to 120°C, preferably at from 15° to 50°C.

The reaction is in general carried out under normal pressure.

To carry out the process, the starting compounds are in most cases employed in equimolar amounts. An excess of one or other reactant produces no substantial advantages. The reaction is preferably carried out in the presence of one of the above-mentioned solvents, at the indicated temperatures; after stirring for several hours, the reaction mixture is worked up in the usual manner.

The compounds according to the invention are in most cases obtained in the form of colorless or slightly colored, water-insoluble oils which in some cases cannot be distilled without decomposition but can be freed of the last volatile constituents by so-called "slight distillation", that is to say by prolonged heating under reduced pressure to moderately elevated temperatures, and can in this way be purified. The refractive index, in particular, serves to characterize the compounds.

As has already been mentioned, the new S-(alkoxycarbonyl)-alkyl-thiophosphoric acid ester amides are distinguished by an outstanding insecticidal and acaricidal activity against plant pests, pests harmful to health and pests of stored products. They possess a good action against both sucking and biting insects and against mites (Acarina). At the same time they have a low phytotoxicity and many representatives in addition possess only a low toxicity to warm-blooded animals. For these reasons, the compounds according to the invention may be successfully employed as pesticides in plant protection and the protection of stored products, and in the hygiene field.

To the sucking insects there belong, in the main, aphids (Aphidae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the norther corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (Periplaneta americana), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Acheta domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acari) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the compounds of this invention are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alky arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or rodenticides, fungicides bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1% by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrustation, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

$LD_{100}$ test

Test insects: Sitophilus granarius

Solvent: acetone 2 parts by weight of the active compound were dissolved in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test insects was checked 24 hours after the commencement of the experiments. The destruction in % was determined.

The active compounds, the concentrations of the active compounds, and the results can be seen from the following Table 1:

Table 1
($LD_{100}$ test)

| Active compound | Active-compound concentration of the solution, in % by weight | Destruction in % |
|---|---|---|
| $(C_2H_5O)_2P(=S)-S-CH_2-COOC_2H_5$ (known) (A) | 0.2<br>0.04 | 70<br>10 |
| $(CH_3-NH)(C_2H_5O)P(=S)-S-CH_2-C(=O)-OC_2H_5$ (2) | 0.2<br>0.04 | 100<br>100 |
| $(i-C_3H_7-NH)(C_2H_5O)P(=S)-S-CH_2-C(=O)-OC_2H_5$ (3) | 0.2<br>0.04<br>0.008 | 100<br>100<br>50 |
| $(CH_3-NH)(C_2H_5O)P(=S)-S-CH_2-C(=O)-O-CH(CH_3)_2$ (5) | 0.2<br>0.04 | 100<br>100 |
| $(CH_3-NH)(C_2H_5O)P(=S)-S-CH_2-C(=O)-O-CH(CH_3)(C_2H_5)$ (6) | 0.2<br>0.04 | 100<br>90 |
| $(i-C_3H_7-NH)(C_2H_5O)P(=S)-S-CH_2-C(=O)-O-CH(CH_3)(C_2H_5)$ (7) | 0.2<br>0.04 | 100<br>100 |
| $(CH_3-NH)(C_2H_5O)P(=S)-S-CH_2-C(=O)-O-CH(C_2H_5)_2$ (15) | 0.2<br>0.04 | 100<br>85 |
| $(i-C_3H_7-NH)(C_2H_5O)P(=S)-S-CH_2-C(=O)-O-CH(C_2H_5)_2$ (16) | 0.2<br>0.04 | 100<br>100 |
| $(CH_3-NH)(C_2H_5O)P(=S)-S-CH_2-C(=O)-O-C(CH_3)_3$ (17) | 0.2<br>0.04 | 100<br>90 |
| $(i-C_3H_7-NH)(C_2H_5O)P(=S)-S-CH_2-C(=O)-O-C(CH_3)_3$ (18) | 0.2<br>0.04<br>0.008 | 100<br>100<br>50 |
| $(i-C_3H_7-NH)(C_2H_5O)P(=S)-S-CH_2-C(=O)-O-i-C_3H_7$ (1) | 0.2<br>0.04<br>0.008 | 100<br>100<br>25 |

EXAMPLE 2

$LT_{100}$ test for Diptera
Test insects: Musca domestica
Solvent: acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per cm² of filter paper varied with the concentration of the solution of active compound. About 25 test insects were then placed in the Petri dish and it was covered with a glass lid.

The condition of the test insects was continuously checked. The time which was necessary for 100% destruction was determined.

The active compounds, the concentrations of the active compounds and the periods of time at which there was 100% destruction can be seen from the following Table 2:

Table 2

(LT$_{100}$ test for Diptera)

| Active compound | Active-compound concentration of the solution, in % by weight | LT$_{100}$ |
|---|---|---|
| (B) known: $(CH_3O)_2P(=S)-S-CH(COOC_2H_5)-CH_2COOC_2H_5$ | 0.2<br>0.04 | 150'<br>6 hrs = 80% |
| (2) $CH_3-NH, C_2H_5O-P(=S)-S-CH_2-C(=O)-OC_2H_5$ | 0.2<br>0.04<br>0.008 | 80'<br>240'<br>8 hrs = 80% |
| (3) $i-C_3H_7-NH, C_2H_5O-P(=S)-S-CH_2-C(=O)-OC_2H_5$ | 0.2<br>0.04 | 50'<br>160' |
| (5) $CH_3-NH, C_2H_5O-P(=S)-S-CH_2-C(=O)-O-CH(CH_3)_2$ | 0.2<br>0.04 | 115'<br>210' |
| (6) $CH_3-NH, C_2H_5O-P(=S)-S-CH_2-C(=O)-O-CH(CH_3)(C_2H_5)$ | 0.2<br>0.04 | 105'<br>210' |
| (7) $i-C_3H_7-NH, C_2H_5O-P(=S)-S-CH_2-C(=O)-O-CH(CH_3)(C_2H_5)$ | 0.2<br>0.04 | 105'<br>180' |
| (4) $CH_3-NH, C_2H_5O-P(=S)-S-CH_2-C(=O)-OCH_3$ | 0.2<br>0.04 | 110'<br>240' |
| (10) $i-C_3H_7-NH, C_2H_5O-P(=S)-S-CH_2-C(=O)-O-CH_2-CH(CH_3)_2$ | 0.2<br>0.04 | 120'<br>180' |
| (16) $i-C_3H_7-NH, C_2H_5O-P(=S)-S-CH_2-C(=O)-O-CH(C_2H_5)_2$ | 0.2<br>0.04 | 120'<br>4 hrs |
| (17) $CH_3-NH, C_2H_5O-P(=S)-S-CH_2-C(=O)-O-C(CH_3)_3$ | 0.2<br>0.04<br>0.008 | 60'<br>120'<br>6 hrs = 90% |
| (18) $i-C_3H_7-NH, C_2H_5O-P(=S)-S-CH_2-C(=O)-O-C(CH_3)_3$ | 0.2<br>0.04<br>0.008 | 60'<br>105'<br>6 hrs |
| (22) $i-C_3H_7-NH, C_2H_5O-P(=S)-S-CH_2-C(=O)-O-CH(CH_3)(C_3H_7)$ | 0.2<br>0.04 | 105'<br>4 hrs |
| (1) $i-C_3H_7-NH, C_2H_5O-P(=S)-S-CH_2-C(=O)-O-i-C_3H_7$ | 0.2<br>0.04<br>0.008 | 45'<br>75'<br>4 hrs |

EXAMPLE 3

LT$_{100}$ test for Diptera
Test insects: Aedes aegypti
Solvent: acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per cm² of filter paper varied with the concentration of the solution of active compound. About 25 test insects were then placed in the Petri dish and it was covered with a glass lid.

The condition of the test insects was continuously checked. The time which was necessary for 100% destruction was determined.

The active compounds, the concentrations of the active compounds and the periods of time at which there was 100% destruction can be seen from the following Table 3:

Solvent: 99 parts by weight of acetone
Emulsifier: 1 part by weight of benzylhydroxydiphenyl polyglycol ether To produce a suitable preparation of active compound, 2 parts by weight of the active compound were dissolved in 1,000 parts by volume of the solvent containing the amount of emulsifier stated above. The solution thus obtained was diluted with water to the desired lower concentrations.

The aqueous preparations of the active compounds were placed in glass vessels and about 25 mosquito larvae were then placed in each glass vessel.

After 24 hours, the degree of destruction was determined as a percentage. 100% means that all the larvae Table 3

| Active compound | (LT$_{100}$ test for Diptera) Active-compound concentration of the solution, in % by weight | LT$_{100}$ |
|---|---|---|
| $(C_2H_5O)_2P(S)-S-CH_2-COOC_2H_5$ (known) (A) | 0.2<br>0.04<br>0.008 | 60'<br>120'<br>3 hrs = 0% |
| i-$C_3H_7$-NH, $C_2H_5O$ >P(S)-S-CH$_2$-C(O)-OC$_2$H$_5$ (3) | 0.2<br>0.04<br>0.008 | 60'<br>120'<br>180' |
| i-$C_3H_7$-NH, $C_2H_5O$ >P(S)-S-CH$_2$-C(O)-O-CH(C$_2$H$_5$)-CH$_3$ (7) | 0.2<br>0.04<br>0.008 | 30'<br>45'<br>150' |
| i-$C_3H_7$-NH, $C_2H_5O$ >P(S)-S-CH$_2$-C(O)-O-CH(C$_2$H$_5$)-C$_2$H$_5$ (16) | 0.2<br>0.04<br>0.008<br>0.0016 | 45'<br>60'<br>120'<br>6 hrs |
| $CH_3$-NH, $C_2H_5O$ >P(S)-S-CH$_2$-C(O)-O-C(CH$_3$)$_3$ (17) | 0.2<br>0.04<br>0.008<br>0.0016 | 60'<br>90'<br>180'<br>6 hrs = 80% |
| i-$C_3H_7$-NH, $C_2H_5O$ >P(S)-S-CH$_2$-C(O)-O-C(CH$_3$)$_3$ (18) | 0.2<br>0.04<br>0.008<br>0.0016 | 30'<br>30'<br>75'<br>150' |
| i-$C_3H_7$-NH, $C_2H_5O$ >P(S)-S-CH$_2$-C(O)-O-CH(CH$_3$)-CH(CH$_3$)-CH$_3$ (20) | 0.2<br>0.04<br>0.008 | 60'<br>90'<br>210' |
| i-$C_3H_7$-NH, $C_2H_5O$ >P(S)-S-CH$_2$-C(O)-O-CH(CH$_3$)-C$_3$H$_7$ (22) | 0.2<br>0.04<br>0.008<br>0.0016 | 45'<br>60'<br>150'<br>6 hrs = 60% |
| i-$C_3H_7$-NH, $C_2H_5O$ >P(S)-S-CH$_2$-C(O)-O-i-C$_3$H$_7$ (1) | 0.2<br>0.04<br>0.008<br>0.0016 | 30'<br>30'<br>105'<br>180' |

EXAMPLE 4

Mosquito larvae test
Test insects: Aedes aegypti larvae were killed. 0% means that no larvae at all were killed.

The active compounds, the concentrations of the active compounds, and the results can be seen from the following Table 4:

Table 4

(Mosquito larvae test)

| Active compound | Active-compound concentration of the solution, in ppm | Degree of destruction in % |
|---|---|---|
| (A) (known) $(C_2H_5O)_2P(=S)-S-CH_2-COOC_2H_5$ | 10<br>1 | 100<br>0 |
| (3) $i\text{-}C_3H_7\text{-}NH$, $C_2H_5O$ — $P(=S)-S-CH_2-C(=O)-OC_2H_5$ | 10<br>1<br>0.1 | 100<br>100<br>0 |
| (5) $CH_3\text{-}NH$, $C_2H_5O$ — $P(=S)-S-CH_2-C(=O)-O-CH(CH_3)_2$ | 10<br>1 | 100<br>80 |
| (7) $i\text{-}C_3H_7\text{-}NH$, $C_2H_5O$ — $P(=S)-S-CH_2-C(=O)-O-CH(C_2H_5)CH_3$ | 10<br>1<br>0.1<br>0.01 | 100<br>100<br>100<br>0 |
| (8) $i\text{-}C_3H_7\text{-}NH$, $C_2H_5O$ — $P(=S)-S-CH_2-C(=O)-O-C_5H_{11}$ | 10<br>1<br>0.1 | 100<br>100<br>0 |
| (9) $i\text{-}C_3H_7\text{-}NH$, $C_2H_5O$ — $P(=S)-S-CH_2-C(=O)-O-CH_2-C(CH_3)_2-C_2H_5$ | 10<br>1<br>0.1 | 100<br>100<br>30 |
| (10) $i\text{-}C_3H_7\text{-}NH$, $C_2H_5O$ — $P(=S)-S-CH_2-C(=O)-O-CH_2-CH(CH_3)-CH_3$ | 10<br>1<br>0.1 | 100<br>100<br>30 |
| (11) $CH_3\text{-}NH$, $C_2H_5O$ — $P(=S)-S-CH_2-C(=O)-O-CH[CH(CH_3)_2]_2$ | 10<br>1<br>0.1 | 100<br>100<br>0 |
| (12) $i\text{-}C_3H_7\text{-}NH$, $C_2H_5O$ — $P(=S)-S-CH_2-C(=O)-O-CH[CH(CH_3)_2]_2$ | 10<br>1<br>0.1<br>0.01 | 100<br>100<br>100<br>0 |
| (13) $i\text{-}C_3H_7\text{-}NH$, $C_2H_5O$ — $P(=S)-S-CH_2-C(=O)-O-CH(CH_3)-CH_2-CH(CH_3)-CH_3$ | 10<br>1<br>0.1 | 100<br>100<br>0 |
| (14) $CH_3\text{-}NH$, $C_2H_5O$ — $P(=S)-S-CH_2-C(=O)-O-CH(CH_3)-CH_2-CH(CH_3)-CH_3$ | 10<br>1<br>0.1 | 100<br>100<br>0 |
| (15) $CH_3\text{-}NH$, $C_2H_5O$ — $P(=S)-S-CH_2-C(=O)-O-CH(C_2H_5)_2$ | 10<br>1<br>0.1 | 100<br>100<br>30 |
| (16) $i\text{-}C_3H_7\text{-}NH$, $C_2H_5O$ — $P(=S)-S-CH_2-C(=O)-O-CH(C_2H_5)_2$ | 10<br>1<br>0.1<br>0.01 | 100<br>100<br>100<br>70 |
| (17) $CH_3\text{-}NH$, $C_2H_5O$ — $P(=S)-S-CH_2-C(=O)-O-C(CH_3)_3$ | 10<br>1<br>0.1<br>0.01 | 100<br>100<br>100<br>0 |
| (18) $i\text{-}C_3H_7\text{-}NH$, $C_2H_5O$ — $P(=S)-S-CH_2-C(=O)-O-C(CH_3)_3$ | 10<br>1<br>0.1 | 100<br>100<br>80 |

Table 4-continued

| Active compound | (Mosquito larvae test) Active-compound concentration of the solution, in ppm | Degree of destruction in % |
|---|---|---|
| (19) CH$_3$—NH—P(=S)(OC$_2$H$_5$)—S—CH$_2$—C(=O)—O—CH(CH$_3$)—CH(CH$_3$)—CH$_3$ | 10<br>1<br>0.1 | 100<br>100<br>0 |
| (20) i-C$_3$H$_7$—NH—P(=S)(OC$_2$H$_5$)—S—CH$_2$—C(=O)—O—CH(CH$_3$)—CH(CH$_3$)—CH$_3$ | 10<br>1<br>0.1 | 100<br>100<br>90 |
| (22) i-C$_3$H$_7$—NH—P(=S)(OC$_2$H$_5$)—S—CH$_2$—C(=O)—O—CH(CH$_3$)—C$_3$H$_7$ | 10<br>1<br>0.1<br>0.01 | 100<br>100<br>100<br>0 |
| (1) i-C$_3$H$_7$—NH—P(=S)(OC$_2$H$_5$)—S—CH$_2$—C(=O)—O—i-C$_3$H$_7$ | 10<br>1<br>0.1 | 100<br>100<br>0 |

EXAMPLE 5

Plutella test
Solvent: 3 parts by weight acetone
Emulsifier: 1 part by weight alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all of the caterpillars were killed whereas 0% means that none of the caterpillars were killed.

The active compounds, the concentrations of the active compounds, the evaluation times and the results can be seen from the following Table 5:

Table 5

| Active compound | (Plutella test) Active-compound concentration in % by weight | Degree of destruction in % after 3 days |
|---|---|---|
| (A) (known) (C$_2$H$_5$O)$_2$P(=S)—S—CH$_2$—CO—OC$_2$H$_5$ | 0.1 | 0 |
| (1) i-C$_3$H$_7$—NH—P(=S)(OC$_2$H$_5$)—S—CH$_2$—C(=O)—O—i-C$_3$H$_7$ | 0.1<br>0.01 | 100<br>100 |
| (17) CH$_3$—NH—P(=S)(OC$_2$H$_5$)—S—CH$_2$—C(=O)—O—C(CH$_3$)$_3$ | 0.1<br>0.01 | 100<br>100 |
| (18) i-C$_3$H$_7$—NH—P(=S)(OC$_2$H$_5$)—S—CH$_2$—C(=O)—O—C(CH$_3$)$_3$ | 0.1<br>0.01<br>0.001 | 100<br>100<br>75 |
| (12) i-C$_3$H$_7$—NH—P(=S)(OC$_2$H$_5$)—S—CH$_2$—C(=O)—O—CH(CH(CH$_3$)$_2$)$_2$ | 0.1<br>0.01 | 100<br>85 |
| (16) i-C$_3$H$_7$—NH—P(=S)(OC$_2$H$_5$)—S—CH$_2$—C(=O)—O—CH(C$_2$H$_5$)$_2$ | 0.1<br>0.01 | 100<br>85 |

Table 5-continued

| Active compound | (Plutella test) Active-compound concentration in % by weight | Degree of destruction in % after 3 days |
|---|---|---|
| (24) $C_2H_5O\diagdown_P\diagup^O$ <br> $CH_3-NH\diagup\phantom{P}\diagdown S-CH_2-C-O-i-C_3H_7$ <br> $\phantom{CH_3-NH\diagup\phantom{P}\diagdown S-CH_2-C-O-i}\|\phantom{-}$ <br> $\phantom{CH_3-NH\diagup\phantom{P}\diagdown S-CH_2-C-O-i}O$ | 0.1 <br> 0.01 | 100 <br> 60 |
| (23) $C_2H_5O\diagdown_P\diagup^O$ <br> $i\text{-}C_3H_7-NH\diagup\phantom{P}\diagdown S-CH_2-C-O-i-C_3H_7$ <br> $\phantom{i\text{-}C_3H_7-NH\diagup\phantom{P}\diagdown S-CH_2-C-O-i}\|\phantom{-}$ <br> $\phantom{i\text{-}C_3H_7-NH\diagup\phantom{P}\diagdown S-CH_2-C-O-i}O$ | 0.1 <br> 0.01 | 100 <br> 100 |
| (25) $C_2H_5O\diagdown_P\diagup^S$ <br> $i\text{-}C_3H_7-NH\diagup\phantom{P}\diagdown S-CH-CO-O-C_2H_5$ <br> $\phantom{i\text{-}C_3H_7-NH\diagup\phantom{P}\diagdown S-}\|\phantom{CO-O-C_2H_5}$ <br> $\phantom{i\text{-}C_3H_7-NH\diagup\phantom{P}\diagdown S-}CH_2-CO-O-C_2H_5$ | 0.1 <br> 0.01 | 100 <br> 70 |
| (27) $C_2H_5O\diagdown_P\diagup^O$ <br> $i\text{-}C_3H_7-NH\diagup\phantom{P}\diagdown S-CH-CO-O-C_2H_5$ <br> $\phantom{i\text{-}C_3H_7-NH\diagup\phantom{P}\diagdown S-}\|\phantom{CO-O-C_2H_5}$ <br> $\phantom{i\text{-}C_3H_7-NH\diagup\phantom{P}\diagdown S-}CH_2-CO-O-C_2H_5$ | 0.1 <br> 0.01 | 100 <br> 50 |

EXAMPLE 6

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*), which had been heavily infested with peach aphids (*Myzus persicae*), were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following Table 6:

Table 6

| Active compound | (Myzus test) Active-compound concentration in % by weight | Degree of destruction in % after 1 day |
|---|---|---|
| (A) $C_2H_5O\diagdown_P\diagup^S$ <br> $C_2H_5O\diagup\phantom{P}\diagdown-S-CH_2-CO-OC_2H_5$ <br> (known) | 0.1 <br> 0.01 | 50 <br> 0 |
| (3) $i\text{-}C_3H_7-NH\diagdown_P\diagup^S$ <br> $C_2H_5O\diagup\phantom{P}\diagdown S-CH_2-C\diagup^O\diagdown_{OC_2H_5}$ | 0.1 <br> 0.01 <br> 0.001 | 100 <br> 90 <br> 30 |
| (1) $i\text{-}C_3H_7-NH\diagdown_P\diagup^S$ <br> $C_2H_5O\diagup\phantom{P}\diagdown S-CH_2-C\diagup^O\diagdown_{O-i\text{-}C_3H_7}$ | 0.1 <br> 0.01 <br> 0.001 | 100 <br> 95 <br> 60 |
| (17) $CH_3-NH\diagdown_P\diagup^S$ <br> $C_2H_5O\diagup\phantom{P}\diagdown S-CH_2-C\diagup^O\diagdown_{O-C(CH_3)_3}$ | 0.1 <br> 0.01 | 100 <br> 70 |
| (18) $i\text{-}C_3H_7-NH\diagdown_P\diagup^S$ <br> $C_2H_5O\diagup\phantom{P}\diagdown S-CH_2-C\diagup^O\diagdown_{O-C(CH_3)_3}$ | 0.1 <br> 0.01 <br> 0.001 | 100 <br> 99 <br> 30 |
| (20) $i\text{-}C_3H_7-NH\diagdown_P\diagup^S$ <br> $C_2H_5O\diagup\phantom{P}\diagdown S-CH_2-C\diagup^O\diagdown_{O-CH-CH-CH_3}$ <br> $\phantom{C_2H_5O\diagup\phantom{P}\diagdown S-CH_2-C\diagup^O\diagdown_{O-}}H_3C\phantom{-}CH_3$ | 0.1 <br> 0.01 | 100 <br> 40 |
| (16) $i\text{-}C_3H_7-NH\diagdown_P\diagup^S$ <br> $C_2H_5O\diagup\phantom{P}\diagdown S-CH_2-C\diagup^O\diagdown_{O-CH-C_2H_5}$ <br> $\phantom{C_2H_5O\diagup\phantom{P}\diagdown S-CH_2-C\diagup^O\diagdown_{O-}}\phantom{-}C_2H_5$ | 0.1 <br> 0.01 | 98 <br> 40 |

Table 6-continued

| Active compound | (Myzus test) Active-compound concentration in % by weight | Degree of destruction in % after 1 day |
|---|---|---|
| 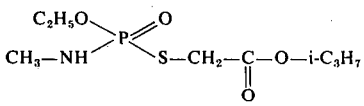 (24) | 0.1<br>0.01 | 100<br>70 |
| 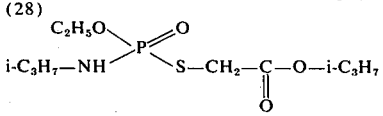 (28) | 0.1<br>0.01 | 100<br>95 |
| 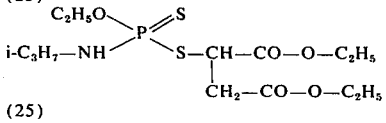 (23) | 0.1<br>0.01<br>0.001 | 100<br>100<br>30 |
| 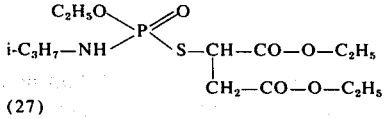 (25) | 0.1<br>0.01<br>0.001 | 100<br>100<br>65 |
| 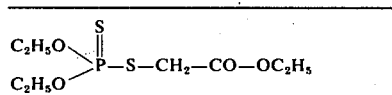 (27) | 0.1<br>0.01 | 100<br>98 |

EXAMPLE 7

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained is expressed as a percentage: 100% means that all the spider mites were killed whereas 0% means that none of the spider mites were killed.

The active compounds, the concentrations of the active compounds, the evaluation times and the results can be seen from the following Table 7:

Table 7

| Active compound | (Tetranychus test/resistant) Active-compound concentration in % by weight | Degree of destruction in % after 2 days |
|---|---|---|
| 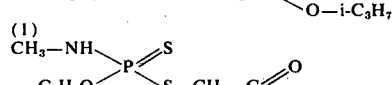 (known) (A) | 0.1 | 0 |
| 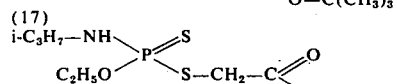 (1) | 0.1<br>0.01 | 100<br>40 |
| (17) | 0.1<br>0.01 | 100<br>60 |
| (18) | 0.1<br>0.01 | 100<br>80 |
| 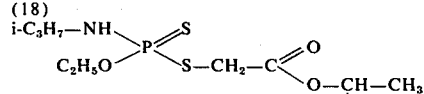 (7) | 0.1 | 100 |
| 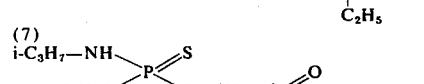 (22) | 0.1 | 99 |

Table 7-continued

| Active compound | (Tetranychus test/resistant) Active-compound concentration in % by weight | Degree of destruction in % after 2 days |
|---|---|---|
| (11) CH$_3$—NH—P(=S)(—OC$_2$H$_5$)—S—CH$_2$—C(=O)—O—CH(CH(CH$_3$)$_2$)$_2$ | 0.1 | 100 |
| (12) i-C$_3$H$_7$—NH—P(=S)(—OC$_2$H$_5$)—S—CH$_2$—C(=O)—O—CH(CH(CH$_3$)$_2$)$_2$ | 0.1 | 100 |
| (16) i-C$_3$H$_7$—NH—P(=S)(—OC$_2$H$_5$)—S—CH$_2$—C(=O)—O—CH(C$_2$H$_5$)$_2$ | 0.1<br>0.01 | 100<br>90 |
| (28) C$_2$H$_5$O—P(=O)(—NH—CH$_3$)—S—CH(CO—O—C$_2$H$_5$)—CH$_2$—CO—O—C$_2$H$_5$ | 0.1<br>0.01 | 100<br>35 |
| (23) C$_2$H$_5$O—P(=O)(—NH—i-C$_3$H$_7$)—S—CH$_2$—C(=O)—O—i-C$_3$H$_7$ | 0.1<br>0.01 | 100<br>40 |
| (25) C$_2$H$_5$O—P(=S)(—NH—i-C$_3$H$_7$)—S—CH(CO—O—C$_2$H$_5$)—CH$_2$—CO—O—C$_2$H$_5$ | 0.1 | 98 |
| (27) C$_2$H$_5$O—P(=O)(—NH—i-C$_3$H$_7$)—S—CH(CO—O—C$_2$H$_5$)—CH$_2$—CO—O—C$_2$H$_5$ | 0.1 | 97 |

The process of this invention is illustrated in the following preparative Example.

EXAMPLE 8

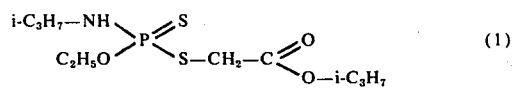

(1)

21.5 g. (0.15 mole) of chloroacetic acid isopropyl ester were added dropwise at room temperature to a solution of 46.2 g (0.18 mole) of the potassium salt of O-ethyl-N-isopropylamido-dithiophosphoric acid in 300 ml of acetonitrile. The reaction took place slightly exothermically. The reaction mixture was stirred overnight at 50°C and then poured into water; the product was taken up in dichloromethane and the organic phase was washed with water, dried over sodium sulfate and filtered. The filtrate was concentrated. S-(isopropoxycarbonyl)-methyl-O-ethyl-N-isopropyl-dithiophosphoric acid ester amide was obtained as a yellow oil of refractive index $n_D^{20}$ of 1.5064. The yield was 38.3 g (85.5% of theory).

The following compounds were obtained by methods analogous to that described above.

| Formula | | Physical data | |
|---|---|---|---|
| CH$_3$—NH—P(=S)(—OC$_2$H$_5$)—S—CH$_2$—C(=O)—OC$_2$H$_5$ | (2) | B.p.<br>$n_D^{22.5}$ | 135°C/0.02 mm Hg<br>1.5307 |
| i-C$_3$H$_7$—NH—P(=S)(—OC$_2$H$_5$)—S—CH$_2$—C(=O)—OC$_2$H$_5$ | (3) | B.p.<br>$n_D^{21.5}$ | 135°C/0.1 mm Hg<br>1.5119 |
| CH$_3$—NH—P(=S)(—OC$_2$H$_5$)—S—CH$_2$—C(=O)—OCH$_3$ | (4) | $n_D^{20}$ | 1.5344 |
| CH$_3$—NH—P(=S)(—OC$_2$H$_5$)—S—CH$_2$—C(=O)—O—CH(CH$_3$)—CH$_3$ | (5) | $n_D^{21}$ | 1.5142 |

-continued

| Formula | | Physical data | |
|---|---|---|---|
| CH₃—NH\P(=S)/C₂H₅O, S—CH₂—C(=O)—O—CH(CH₃)(C₂H₅) | (6) | $n_D^{20}$ | 1.5122 |
| i-C₃H₇—NH\P(=S)/C₂H₅O, S—CH₂—C(=O)—O—CH(CH₃)(C₂H₅) | (7) | $n_D^{24}$ | 1.5031 |
| i-C₃H₇—NH\P(=S)/C₂H₅O, S—CH₂—C(=O)—O—C₅H₁₁ | (8) | $n_D^{20}$ | 1.5029 |
| i-C₃H₇—NH\P(=S)/C₂H₅O, S—CH₂—C(=O)—O—CH₂—C(CH₃)₂—C₂H₅ | (9) | $n_D^{20}$ | 1.5016 |
| i-C₃H₇—NH\P(=S)/C₂H₅O, S—CH₂—C(=O)—O—CH₂—CH(CH₃)—CH₃ | (10) | $n_D^{20}$ | 1.5040 |
| CH₃—NH\P(=S)/C₂H₅O, S—CH₂—C(=O)—O—CH[CH(CH₃)₂]₂ | (11) | $n_D^{20}$ | 1.5073 |
| i-C₃H₇—NH\P(=S)/C₂H₅O, S—CH₂—C(=O)—O—CH[CH(CH₃)₂]₂ | (12) | $n_D^{20}$ | 1.5001 |
| i-C₃H₇—NH\P(=S)/C₂H₅O, S—CH₂—C(=O)—O—CH(CH₃)—CH₂—CH(CH₃)—CH₃ | (13) | $n_D^{20}$ | 1.4949 |
| CH₃—NH\P(=S)/C₂H₅O, S—CH₂—C(=O)—O—CH(CH₃)—CH₂—CH(CH₃)—CH₃ | (14) | $n_D^{20}$ | 1.5051 |
| CH₃—NH\P(=S)/C₂H₅O, S—CH₂—C(=O)—O—CH(C₂H₅)₂ | (15) | $n_D^{20}$ | 1.5106 |
| i-C₃H₇—NH\P(=S)/C₂H₅O, S—CH₂—C(=O)—O—CH(C₂H₅)₂ | (16) | $n_D^{20}$ | 1.5015 |
| CH₃—NH\P(=S)/C₂H₅O, S—CH₂—C(=O)—O—C(CH₃)₃ | (17) | $n_D^{20}$ | 1.5109 |
| i-C₃H₇—NH\P(=S)/C₂H₅O, S—CH₂—C(=O)—O—C(CH₃)₃ | (18) | $n_D^{20}$ | 1.5038 |
| CH₃—NH\P(=S)/C₂H₅O, S—CH₂—C(=O)—O—CH(CH₃)—CH(CH₃)—CH₃ | (19) | $n_D^{20}$ | 1.5098 |

| Formula | | Physical data | |
|---|---|---|---|
| i-C$_3$H$_7$—NH—P(=S)(OC$_2$H$_5$)—S—CH$_2$—C(=O)—O—CH(CH$_3$)—CH(CH$_3$)—CH$_3$ (with H$_3$C branch) | (20) | $n_D^{20}$ | 1.5011 |
| CH$_3$—NH—P(=S)(OC$_2$H$_5$)—S—CH$_2$—C(=O)—O—CH(CH$_3$)—C$_3$H$_7$ | (21) | $n_D^{20}$ | 1.5095 |
| i-C$_3$H$_7$—NH—P(=S)(OC$_2$H$_5$)—S—CH$_2$—C(=O)—O—CH(CH$_3$)—C$_3$H$_7$ | (22) | $n_D^{20}$ | 1.4995 |
| i-C$_3$H$_7$—NH—P(=O)(OC$_2$H$_5$)—S—CH$_2$—C(=O)—O-i-C$_3$H$_7$ | (23) | $n_D^{20}$ | 1.4727 |
| CH$_3$—NH—P(=O)(OC$_2$H$_5$)—S—CH$_2$—C(=O)—O-i-C$_3$H$_7$ | (24) | $n_D^{20}$ | 1.4782 |
| i-C$_3$H$_7$—NH—P(=S)(OC$_2$H$_5$)—S—CH(CO—O—C$_2$H$_5$)—CH$_2$—CO—O—C$_2$H$_5$ | (25) | $n_D^{20}$ | 1.5029 |
| CH$_3$—NH—P(=S)(OC$_2$H$_5$)—S—CH(CO—O—C$_2$H$_5$)—CH$_2$—CO—O—C$_2$H$_5$ | (26) | $n_D^{20}$ | 1.5062 |
| i-C$_3$H$_7$—NH—P(=O)(OC$_2$H$_5$)—S—CH(CO—O—C$_2$H$_5$)—CH$_2$—CO—O—C$_2$H$_5$ | (27) | $n_D^{20}$ | 1.4757 |
| CH$_3$—NH—P(=O)(OC$_2$H$_5$)—S—CH(CO—O—C$_2$H$_5$)—CH$_2$—CO—O—C$_2$H$_5$ | (28) | $n_D^{20}$ | 1.4790 |
| CH$_2$=CH—CH$_2$—NH—P(=S)(OC$_2$H$_5$)—S—CH$_2$—C(=O)—O—CH(CH$_3$)(C$_2$H$_5$) | (29) | $n_D^{20}$ | 1.5151 |
| CH$_2$=CH—CH$_2$—NH—P(=S)(OC$_2$H$_5$)—S—CH$_2$—C(=O)—O—C(CH$_3$)$_3$ | (30) | $n_D^{20}$ | 1.5145 |
| CH$_2$=CH—CH$_2$—NH—P(=S)(OC$_2$H$_5$)—S—CH$_2$—C(=O)—O—CH(CH$_3$)$_2$ | (31) | $n_D^{20}$ | 1.5168 |
| i-C$_3$H$_7$—NH—P(=S)(OC$_2$H$_5$)—S—CH$_2$—C(=O)—O—CH$_2$—CH=CH$_2$ | (32) | $n_D^{20}$ | 1.5203 |
| i-C$_3$H$_7$—NH—P(=S)(OC$_2$H$_5$)—S—CH(CH$_3$)—C(=O)—O—CH(CH$_3$)$_2$ | (33) | $n_D^{20}$ | 1.5011 |
| i-C$_3$H$_7$—NH—P(=S)(OC$_2$H$_5$)—S—CH(CH$_3$)—C(=O)—O—C(CH$_3$)$_3$ | (34) | $n_D^{20}$ | 1.4984 |

| Formula | | Physical data | |
|---|---|---|---|
| $C_2H_5O$–P(=S)(–NH–$C_2H_5$)–S–$CH_2$–C(=O)–O–CH(CH$_3$)$_2$ | (35) | $n_D^{20}$ | 1.5089 |
| $C_2H_5O$–P(=S)(–NH–$C_2H_5$)–S–$CH_2$–C(=O)–O–CH(CH$_3$)(C$_2$H$_5$) | (36) | $n_D^{20}$ | 1.5068 |
| $C_2H_5O$–P(=S)(–NH–$C_2H_5$)–S–$CH_2$–C(=O)–O–C(CH$_3$)$_3$ | (37) | $n_D^{20}$ | 1.5064 |
| n-$C_3H_7O$–P(=S)(–NH–i-$C_3H_7$)–S–$CH_2$–C(=O)–O–CH(CH$_3$)$_2$ | (38) | $n_D^{20}$ | 1.5028 |
| n-$C_3H_7O$–P(=S)(–NH–i-$C_3H_7$)–S–$CH_2$–C(=O)–O–CH(CH$_3$)(C$_2$H$_5$) | (39) | $n_D^{20}$ | 1.5004 |
| n-$C_3H_7O$–P(=S)(–NH–i-$C_3H_7$)–S–$CH_2$–C(=O)–O–C(CH$_3$)$_3$ | (40) | $n_D^{20}$ | 1.4989 |
| i-$C_3H_7O$–P(=S)(–NH–CH$_3$)–S–$CH_2$–C(=O)–O–CH(CH$_3$)$_2$ | (41) | $n_D^{20}$ | 1.5087 |
| i-$C_3H_7O$–P(=S)(–NH–CH$_3$)–S–$CH_2$–C(=O)–O–CH(CH$_3$)(C$_2$H$_5$) | (42) | $n_D^{20}$ | 1.5068 |
| i-$C_3H_7O$–P(=S)(–NH–CH$_3$)–S–$CH_2$–C(=O)–O–C(CH$_3$)$_3$ | (43) | $n_D^{20}$ | 1.5055 |
| i-$C_3H_7O$–P(=S)(–NH–i-$C_3H_7$)–S–$CH_2$–C(=O)–O–CH(CH$_3$)$_2$ | (44) | $n_D^{20}$ | 1.4870 |
| i-$C_3H_7O$–P(=S)(–NH–i-$C_3H_7$)–S–$CH_2$–C(=O)–O–CH(CH$_3$)(C$_2$H$_5$) | (45) | $n_D^{20}$ | 1.4849 |
| i-$C_3H_7O$–P(=S)(–NH–i-$C_3H_7$)–S–$CH_2$–C(=O)–O–C(CH$_3$)$_3$ | (46) | $n_D^{20}$ | 1.4843 |

It will be appreciated that the instant specification and examples are set forth by way of illustration and not limitation, and that various modifications and changes may be made without departing from the spirit and scope of the present invention.

What is claimed is:

1. An S-(alkoxycarbonyl)-alkyl-thiophosphoric acid ester amide of the formula

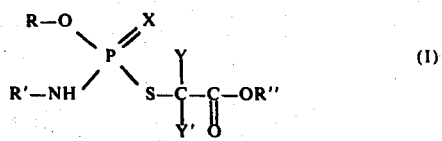

in which

R, R' and R'' each independently is alkyl of 1 to 10 carbon atoms or lower alkenyl, Y is hydrogen or lower alkyl, Y' is hydrogen, lower alkyl or —CH$_2$—CO—OR'',
and
X is oxygen or sulfur.

2. A compound according to claim 1, in which R and R' each independently is lower alkyl or allyl; R'' is alkyl of 1 to 8 carbon atoms or allyl; Y is hydrogen; and Y' is hydrogen, methyl or —CH$_2$—CO—OR''.

3. The compound according to claim 1 wherein such compound is S-(isopropoxycarbonyl)-methyl-O-ethyl-N-isopropyl-dithiophosphoric acid ester amide of the formula

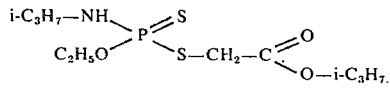 (1)

4. The compound according to claim 1 wherein such compound is S-(isopropoxycarbonyl)-methyl-O-ethyl-N-methyl-dithiophosphoric acid ester amide of the formula

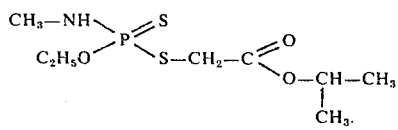 (5)

5. The compound according to claim 1 wherein such compound is S-(t-butoxycarbonyl)-methyl-O-ethyl-N-isopropyl-dithiophosphoric acid ester amide of the formula

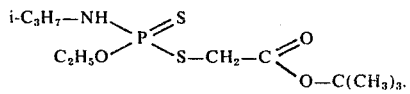 (18)

6. The compound according to claim 1 wherein such compound is S-(1-methyl-butoxycarbonyl)-methyl-O-ethyl-N-isopropyl-dithiophosphoric acid ester amide of the formula

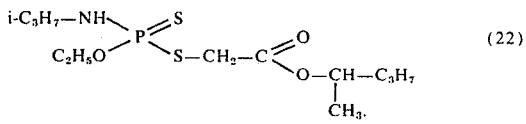 (22)

7. The compound according to claim 1 wherein such compound is S-(isopropoxycarbonyl)-methyl-O-ethyl-N-isopropyl-thiolphosphoric acid ester amide of the formula

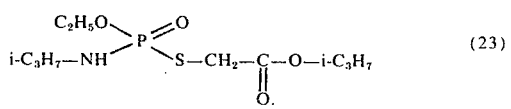 (23)

8. The compound according to claim 1 wherein such compound is S-[1,2-di-(ethoxycarbonyl)-ethyl]-O-ethyl-N-isopropyl-dithiophosphoric acid ester amide of the formula

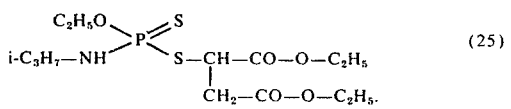 (25)

* * * * *